United States Patent [19]

Gobran

[11] 4,237,889
[45] Dec. 9, 1980

[54] DIAPER CLOSURE UTILIZING PRESSURE-SENSITIVE ADHESIVE TAPE HAVING TEXTURED FOIL BACKING

[75] Inventor: Ramsis Gobran, Roseville, Minn.

[73] Assignee: Minnesota Mining and Manufacturing Company, Saint Paul, Minn.

[21] Appl. No.: 942,026

[22] Filed: Sep. 13, 1978

Related U.S. Application Data

[63] Continuation-in-part of Ser. No. 842,058, Oct. 14, 1977, abandoned.

[51] Int. Cl.³ .............................................. A61F 13/16
[52] U.S. Cl. ...................................... 128/287; 428/40; 428/43; 428/167; 428/343; 428/906
[58] Field of Search ................... 428/40, 167, 43, 172, 428/343, 906, 523; 128/284, 287

[56] References Cited
U.S. PATENT DOCUMENTS

| | | | |
|---|---|---|---|
| 3,630,201 | 12/1971 | Endres | 428/40 |
| 3,950,480 | 4/1976 | Adams et al. | 264/284 |
| 3,985,136 | 10/1976 | Cepuntis | 128/284 |
| 4,014,339 | 3/1977 | Tritsch | 128/287 |

FOREIGN PATENT DOCUMENTS

| | | | |
|---|---|---|---|
| 748460 | 5/1970 | Belgium | 428/523 |
| 50-13306 | 5/1975 | Japan | 428/906 |
| 943670 | 12/1963 | United Kingdom | 428/523 |

*Primary Examiner*—Stanley S. Silverman
*Attorney, Agent, or Firm*—Cruzan Alexander; Donald M. Sell; Richard E. Brink

[57] ABSTRACT

Pressure-sensitive adhesive tape, having an untensilized crystalline isotactic polypropylene or linear high density polyethylene film backing with a pattern of alternating ridges and valleys on one side, is especially adapted for use as a tab closure for diapers. The ridges are so disposed that, when a tab is cut from the tape, at least some of the ridges extend at an angle of 60° or less to the lateral edge of the tab, thereby minimizing any tendency toward inadvertent tearing.

5 Claims, 12 Drawing Figures

DIAPER CLOSURE UTILIZING PRESSURE-SENSITIVE ADHESIVE TAPE HAVING TEXTURED FOIL BACKING

CROSS-REFERENCE TO RELATED APPLICATION

This application is a continuation-in-part of application Ser. No. 842,058, filed Oct. 14, 1977, now abandoned.

TECHNICAL FIELD

This invention relates to normally tacky and pressure-sensitive adhesive tape, especially to tape having a polyolefin foil backing.

The presently contemplated major use for tapes of the invention is in the fastening of diapers, especially disposable diapers.

BACKGROUND ART

During approximately the last decade, short strips, or tabs, of normally tacky and pressure-sensitive adhesive tape have replaced safety pins as the means for closing disposable diapers. Prior to the present invention, each known tape had its own unique advantages and disadvantages, no such tape proving completely satisfactory.

Heretofore, the most widely used tape for diaper closures comprised a paper backing treated with a moisture-resistant polymer, provided on one face with a normally tacky and pressure-sensitive adhesive and on the other face with a release coating. Paper is a surprisingly expensive material, and its cost is increased by the several treatments to which it is subjected in preparing a tape suitable for diaper closure use. Even treated paper retains a moisture-sensitivity which occasionally weakens it sufficiently to cause it to fail when used as the backing in a tape closure for a diaper worn by an active baby. Further, paper is comparatively stiff, so that the edge of a paper tape closure may injure a baby's tender skin. An additional problem arises if the edge of the closure is inadvertently nicked, as may occur during the process of cutting tabs from a roll of tape prior to attaching them to diapers. It has been found that when such an edge-nicked tab is subjected to twisting tensile forces by an active infant, a tear often propagates across the tab, commencing at the weakened nicked edge.

Cloth is more attractive, flexible and tear-resistant than paper, but the process of weaving it is expensive, special treatments are required to prevent the penetration of adhesive when it is used as a tape backing, and there is a tendency for it to ravel. Various types of non-woven backings, including the so-called "spunbonded" polymeric backings, are less expensive to make and more ravel-resistant than cloth, but their thickness, tear-resistance, etc. are not uniform; further, their open nature makes it both difficult and expensive to apply an adhesive coat.

For many years, various polymeric foils have been employed as the backings for normally tacky and pressure-sensitive adhesive tape. Some such tape has been suggested for use in connection with diapers; see, e.g., U.S. Pat. Nos. 2,002,368, 3,630,201 and 3,937,221. Although polymeric foils may be comparatively inexpensive, when conventional foil-backed tape is used as a diaper closure, it displays one or more of such disadvantages as excessive stiffness (which increases the difficulty of preparing closure strips and causes discomfort to the wearer), or poor resistance to tearing across the closure when subjected to tensile stress along the length of the closure, especially if one edge is inadvertently nicked.

Disposable diapers have a moisture-permeable inner foil liner which contacts the baby, a moisture-absorbent central fluff layer, and a moisture-impermeable outer foil cover (usually polyethylene). A tape closure is typically adhered to the cover on both of two juxtaposed or overlapping diaper portions. Such closures adhere strongly to the foil and thus generally cannot be pulled loose without tearing the cover; while closures are often opened in this way, the central layer is thereby exposed, permitting the inner fluff to fall out. An alternative way to open the closure is to cut or tear it across its length. Since heretofore a closure which could be easily torn when the diaper was removed might inadvertently be prematurely torn by an active diapered baby, it has often been preferred to have a closure which could be cut with a scissors but not readily torn. On the other hand, when a scissors is not available, and the closure cannot be torn, the diaper cover is frequently ripped open, with the undesirable results previously mentioned.

SUMMARY OF INVENTION

The present invention provides tapes which are attractive in appearance, flexible, comparatively inexpensive, and resistant to moisture. Diaper closure tabs formed from these tapes also resist inadvertent cross-tearing when subjected to tensile stress, even if the edge is nicked. At the same time, they can be readily torn across their width when the diaper closed by the tabs is to be removed from the wearer. Such tabs thus combine the advantages possessed by each of the previously employed diaper closures while avoiding their disadvantages.

The invention comprises pressure-sensitive adhesive sheet material in which the backing is a substantially untensilized, tough, ductile foil of isotactic polypropylene or linear high density polyethylene having a fine grain crystal structure; polypropylene is preferred because its higher heat distortion temperature makes it somewhat easier to process on conventional tape-making equipment. (The terms "tough", "ductile" and "fine grain crystal structure" are related to the method of foil formation, it being known that such properties result from the quick quenching of crystalline polymer foils. The term "untensilized" means that the foil has been subjected to no machine direction or cross direction stretching after extrusion but does not preclude such molecular alignment as may occur during the process of extrusion.) The polymer may, and preferably does, include dyes, pigments, or fillers to impart a desired appearance to the end product. The foil has a calipered thickness of about 100–500 micrometers, with one smooth face and one textured face, the latter exhibiting specific physical features.*

*By utilizing crystalline isotactic polypropylene or high density polyethylene and carefully controlling such processing variables as foil thickness, cooling roll temperature and rate of extrusion, it is possible to make tear-resistant tape utilizing a foil backing in which both faces are smooth; however, tapes made in accordance with the present invention not only have higher tear resistance and greater flexibility than identically prepared smooth-faced foil of the same weight per unit area but also have a significantly more attractive appearance.

The pressure-sensitive adhesive is coated over and firmly bonded to one face, using conventional priming techniques if it is considered necessary or desirable; likewise, if it is considered necessary or desirable, a release coating is applied to the other face. It is generally preferred to coat the adhesive over the smooth face, not only because the surface of the adhesive will be more nearly planar but also because the textured surface feels somewhat like cloth and is more aesthetically appealing.

The textured face displays a pattern of elevated areas, or comparatively thick portions, separated by valleys, or comparatively thin portions. The elevated areas take the form of elongate mounds, bosses, or other protuberances (for convenience, all hereinafter referred to as "ridges"), which may be either uniform or varied in shape and dimensions, and may be distributed in either a regular or random pattern. It is important, however, that the ridges be so disposed that when a diaper tab is cut from the tape, at least a plurality of ridges extend at an angle of 60° or less to the lateral edges of the tab, thereby blocking any continuous path of potential tearing along valleys extending within an angle of ±30° from perpendicular to the lateral edges of the tab. It also appears that any such ridge should have a length significantly greater than the width of the valley which it blocks.

As will be shown, a wide variety of patterns meet the foregoing criteria, and foils having such patterns can be successfully used as the backing for tear-resistant diaper closure tape tabs. In the presently preferred form of the invention, however, the textured face displays a random pattern of elongate ridges separated by valleys, the crests of adjacent ridges being 250-1500 micrometers apart and none of the crests being more than either 100 micrometers or $\frac{2}{3}$ of the caliper thickness of the foil below the crest of the highest ridge. The thickness of the foil between the bottom of the valleys and the smooth face is at least 25 micrometers but not more than $\frac{2}{3}$ the calipered thickness. The void volume included on the textured face constitutes 10-60% the apparent volume of the foil.

Foil for use in the invention is prepared according to such well-known extrusion techniques as are shown in U.S. Pat. No. 3,175,026, the disclosure of which is incorporated by reference. The foil is made by extruding a molten polymer through a slot extrusion die and thence into the nip between a silicone rubber-covered support and a water-cooled metal chill roll, the latter being surfaced with a negative of the desired textured pattern. While chrome-plated negatively engraved steel rolls are standard items of commerce, only a small percentage of the thousands of available patterns are useful in preparing a foil suitable for the present invention. In this regard, attention is also directed to the following illustrative U.S. Pat. Nos. showing embossed foil, some suggesting its use as a cover for disposable diapers or as a release sheet for pressure-sensitive tape diaper closures: 3,630,201, 3,832,267, 3,849,050 and 3,950,480. None of these patents discloses a foil suitable for use in practicing the present invention.

As previously indicated, foil of the type described is converted into tape by applying a layer of normally tacky and pressure-sensitive adhesive to one face, using conventional priming techniques as required. The adhesive may be transparent or, if desired, colored by incorporating dyes and pigments in conventional manner. Where the tape is to be used in making closures for disposable diapers, it is important that the adhesive be capable of bonding firmly to the diaper cover, which is usually polyethylene foil. Rubber-resin type pressure-sensitive adhesives are well-suited for this purpose, the "rubber" being either natural rubber or a synthetic block copolymer. The type and amount of resin employed will depend on both the rubber and the degree of adhesiveness desired, appropriate adjustments being readily accomplished according to well-known procedures. Acrylate adhesives, e.g., a 94.5:5.5 iso-octyl acrylate:acrylic acid copolymer as disclosed in U.S. Pat. No. Re. 24,906, may also be employed. Similarly, if the tape is to be converted into a closure for conventional cloth diapers, it may be desirable to utilize moisture-resistant adhesives of the type disclosed in U.S. Pat. No. 4,074,004.

If the textured face of the foil is exposed at the back of the tape, the uneven surface inherently possesses a lower affinity for pressure-sensitive adhesives than the smooth face does; nevertheless, it may be desirable to apply a silicone polymer or any of several other conventional release coats thereover to reduce the adhesive-receptivity still further and facilitate unwinding rolls of the tape. The tape, which normally is made on wide sheets of foil, is then slit to desired widths and lengths and wound convolutely around cores. Diaper closures are formed by cutting appropriately-sized strips (e.g., 2.5×7.5 cm) from the tape.

Although it is generally preferred to coat the pressure-sensitive adhesive on the smooth face of the foil, there are certain advantages to coating the adhesive on the textured face. For example, the exposed surface of the adhesive will then contact the smooth back side of the foil when the tape is wound in roll form, thereby maintaining a nearly planar surface. Such a planar surface quickly establishes contact with a diaper and bonds firmly and quickly. It has been found desirable to omit pigment from adhesive coated on a textured face, since the cloth-like pattern is then visible through the foil backing.

BRIEF DESCRIPTION OF THE DRAWINGS

As an aid to understanding the invention, attention is directed to the accompanying drawing, in which like numbers refer to like parts in the several views, and in which.

DETAILED DESCRIPTION

Figure 1:
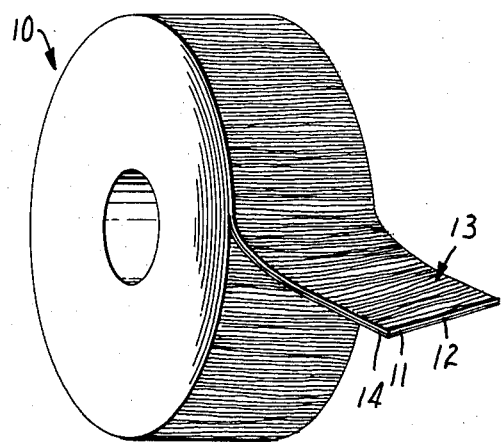
FIG. 1 depicts a roll of polymeric foil-backed pressure-sensitive adhesive tape made in accordance with the invention.
Figure 2:
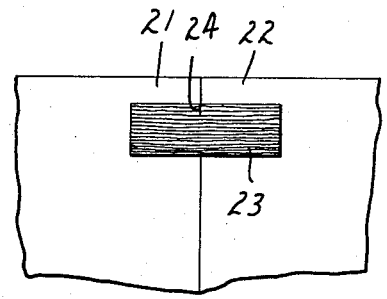
FIG. 2 shows a portion of a disposable diaper, with a closure strip, made by severing a short portion of tape from the roll shown in FIG. 1, adhered to the juxtaposed edges of a diaper.

FIG. 1 illustrates a convolutely wound roll 10 of normally tacky and pressure-sensitive adhesive having polymeric foil backing 11 with smooth face 12 and textured face 13. A layer of normally tacky and pressure-sensitive adhesive 14 is coated over smooth face 12. In FIG. 2, tape diaper closure 23, formed by cutting a comparatively narrow strip across the width direction of the tape of FIG. 1, is adhered to abutted or overlapped diaper edge portions 21 and 22.

The dimensions and configurations of the textured face of the backing are determined by microtoming several cross-sections of foil backing 11 and preparing photo-micrographs. Measurement is then made directly on the photo-micrographs, converting the values obtained to allow for the magnification.

Figure 3:
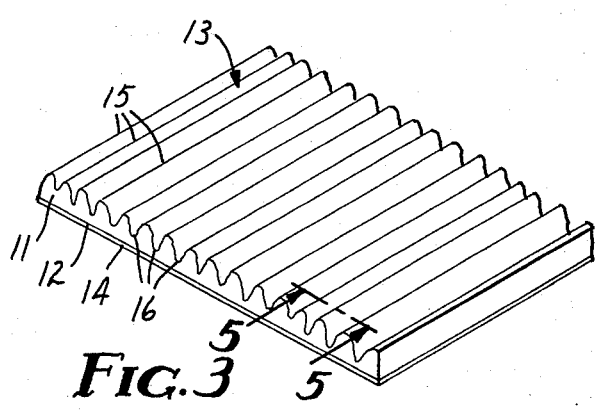
FIG. 3 is an enlarged perspective view taken from one of the corners of the closure of FIG. 2, showing the nature of the textured foil surface.

In FIG. 3, which is an enlarged perspective view of closure 23, textured face 13 is seen to be made up of cordlike ridges 15 and interposed valley portions 16, crests of adjacent ridges being about 250–1500 micrometers apart. While a marginally functional product can be made even if these limits are exceeded somewhat, the resultant product has reduced tensile strength parallel to the ridges and lowered tear resistance perpendicular to the ridges. Not all of the crests are at the same height, but none of them is more than either about 100 micrometers or about $\frac{2}{3}$ the calipered thickness of the foil below the crests of the highest ridge. Again, if these limits are exceeded, the strength is lowered to an undesirable level. Similarly, the valleys are not of constant depth, but the thickness of the foil between the bottom of each valley 16 and smooth face 12 is at least about 25 micrometers and not more than about $\frac{2}{3}$ the calipered thickness. If the thickness falls below this range, the foil lacks the desired degree of strength; if the thickness falls above this range, the foil exceeds the desired stiffness.

The caliper of foil 11 is measured with a conventional thickness gauge in which a pair of opposed feet respectively contact smooth face 12 and textured face 13, the foot contacting the latter surface being sufficiently broad to span several ridges 15 and thus lie in a plane tangential to the highest crests. The apparent volume of a unit area of foil is calculated as the product of area and calipered thickness. The calipered thickness of foil 11 is, of course, greater than the thickness of a foil having the same volume of polymer but with two smooth parallel faces. Knowing the specific gravity of the particular foil-forming composition and the calipered thickness of the foil, the percentage of the apparent volume which actually constitutes voids can readily be calculated. As previously pointed out, the void volume constitutes about 10–60% the apparent volume of the foil. If the void volume falls below 10% of the apparent valume, the foil tends to possess the characteristics of conventional foil. On the other hand, if the void volume exceeds 60% of the apparent volume, the foil lacks the desired degree of strength.

In closure 23 ridges 15 in textured face 13 extend parallel to the direction of the length of closure 23. It has been found that even when a lateral edge of closure 23 is inadvertently nicked, ridges 15 substantially reduce any tendency to tear. It will be recognized that the roll of tape 10 in FIG. 1 could have been formed in a narrow width, with ridges extending parallel to the lateral sides of the tape; in this event, closures 23 would be formed simply by cutting the tape into appropriate lengths.

Figure 4:
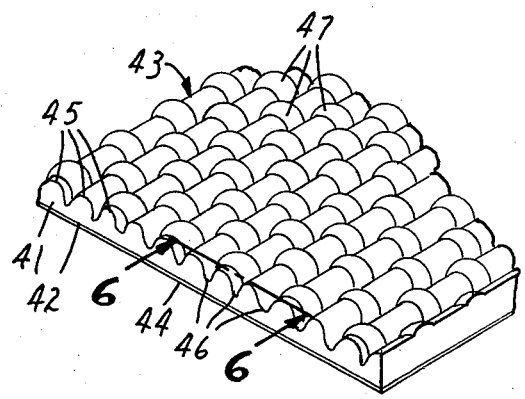
FIG. 4 is a perspective view similar to FIG. 3 but illustrating a somewhat different type of textured foil surface.
Figure 5:
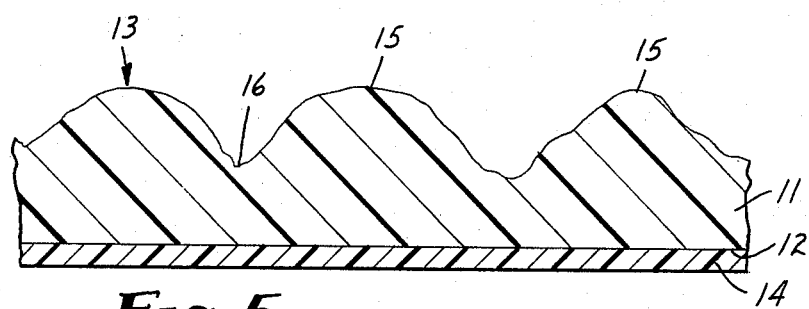
FIG. 5 is a further enlarged cross-sectional view of the closure shown in FIG. 3, taken along section line 5—5, looking in the direction of the arrows.
Figure 6:
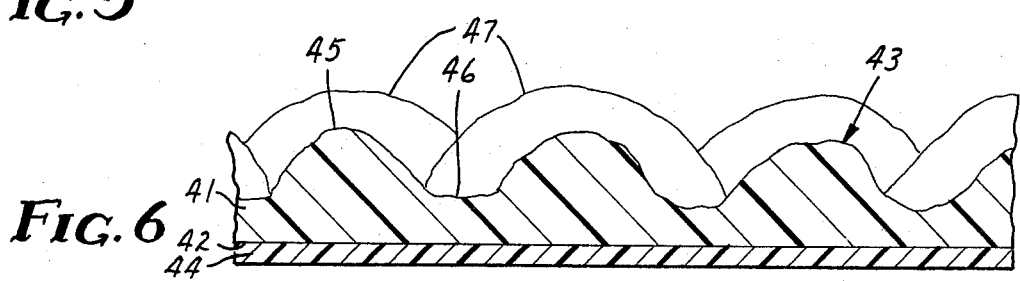
FIG. 6 is a further enlarged cross-sectional view of the closure shown in FIG. 4, taken along section line 6—6, looking in the direction of the arrows.

FIG. 4 depicts a closure substantially similar to that of FIG. 3 but having a modified textured face. Foil backing 41 includes smooth face 42 and textured face 43, a layer of normally tacky and pressure-sensitive adhesive 44 being coated over and bonded to smooth face 42. Textured face 43 includes ridges 45 having alternating valleys 46, similar to ridges 15 and valleys 16 shown in FIG. 3. Extending across each individual ridge 45, at intervals of 700–1000 micrometers, are comparatively short (500–800 micrometers) ribs 47, which alternate in position on ridges 45 and therewith closely simulate the appearance of woven cloth; there are typically about 150–200 ribs 47 per square centimeter. Ribs 47 are believed to reduce any tendency of foil 41 to split or tear along valleys 46 and additionally to reduce the possibility of including air between adjacent layers in a convolutely wound roll of tape. In some circumstances, it is believed that such included air may oxidize the pressure-sensitive adhesive and decrease its effectiveness.

TEST PROCEDURES

As previously noted, a number of tests have proved empirically helpful in defining physical characteristics possessed by satisfactory material. Each of these tests will now be discussed briefly.

Tensile Strength

A 25.4-mm × 150-mm strip of foil, the ridges extending parallel to the 150-mm dimension, is mounted in a tensile testing machine with the upper and lower jaws 75 mm apart. The jaws are then separated at the rate of 127 mm/minute until the yield point is reached. Further details of this conventional test are shown in U.S. Federal Test Method Standard 147C, Method 30.2. Empirically it has been found that the tensile strength at yield for closures of the invention should be at least about 2.5 kg/cm width, a much lower value than is required for paper closures. If the tensile strength falls significantly below 2.5 kg/cm, however, the closure tends to stretch while being attached to a diaper.

Stiffness

A test specimen 3.8 cm wide and 7 cm long is obtained, the long dimension parallel to the direction in which it is desired to measure the bending moment. The strip is mounted in a specimen clamp so that the major portion of its length extends and the bending moment required to flex it ±15° is then determined. Further details of this test are set forth in Test PSTC-37, described in "Test Methods for Pressure-Sensitive Tapes", 6th Edition (1970). It has been empirically determined that, for a closure which is both easy to manufacture and comfortable to wear, the stiffness value should preferably not exceed 3 when measured perpendicular to the long dimension of the closure or 5 when measured parallel to the long dimension of the closure.

Tear Perpetuation Resistance

One end of a specimen approximately 75 mm long and exactly 63 mm wide is positioned in a vertical plane with the long dimension extending horizontally, with the ends of the specimen gripped between a pair of fixed clamps horizontally spaced 2.5 mm from a pair of movable clamps which grip the other end of the test specimen. A 20-mm slit is made in the lower edge of the test specimen between the two pairs of clamps. A pendulum, carrying a circumferential graduated scale, is then allowed to fall freely, tearing the pre-cut test specimen along a continuation of a slit; a frictionally mounted pointer on the scale indicates the grams resistance of the specimen to tearing. Further details of this test are described in Test PSTC-38, in the same "Test Methods for Pressure-Sensitive Tapes" previously mentioned. Test specimens are cut so that the long dimension is parallel to the length of the ultimate diaper closure; hence, this test is useful in predicting the resistance of a diaper closure to tearing when the edge is inadvertently nicked or damaged. It has been empirically determined that the tear perpetuation value across the ridges should be greater than 100 grams. If such values are attained, it may even be desirable to deliberately provide a notch 24 at one or both lateral edges of a diaper closure 23 during manufacture, the stretchable foil and the textured pattern inhibiting accidental tearing but permitting the user to tear the closure when a soiled diaper is to be removed.

PRESENTLY PREFERRED EMBODIMENTS

In the first six tabulated examples which follow, all foil backings were made from commercial crystalline polypropylene polymer (95% isotactic polypropylene, density 0.901, injection molding grade, available from Eastman Chemical Company under the registered trademark designation "Tenite" 4240 and identified in the table as "IPP") into which is blended a small percentage of opacifying $TiO_2$; the polymer is further characterized by a melt temperature of 171°–216° C., a flow rate of 9 g/10 min (as measured by ASTM Test Method D 1238L), and a Vicat softening point of 144° C.* The pattern on the engraved chill roll was varied, as were the melt temperature, foil extrusion speed, and roll temperature, to obtain foils having different caliper and other physical properties. The smooth surface was primed by a conventional corona discharge technique immediately after extrusion. The foil was then allowed to remain at room temperature for about one week to allow the physical properties to reach equilibrium; tensile, stiffness, and tear perpetuation resistance measurements were then made. The smooth surface was subsequently coated with a solution of a conventional rubber-resin pressure-sensitive adhesive and the solvent evaporated to leave approximately 475–500 mg of adhesive per 100 $cm^2$. To facilitate unwinding rolls of tape, an extremely thin layer of conventional "low adhesion backsize", or release coating, was applied to the textured surface in all cases unless otherwise noted.

*The temperature at which a 1-$mm^2$ flat-ended needle under a load of 1000 g penetrates a sample bar 1 mm as the temperature is raised 50° C./hr.

Colored tape having an embossed isotactic polypropylene foil backing, resembling the tab of Example 5 in appearance and utilizing an acrylate-based pressure-sensitive adhesive was sold as a book spine repair tape prior to the present invention. The ridges in this repair tape extended parallel to the machine direction of the foil, the acrylate adhesive would not have possessed high enough shear or adhesion properties, in contact with polyethylene, to be used as a diaper closure tab, and the tear perpetuation resistance was extremely erratic.

Example 7 was essentially identical to Example 5, but the adhesive was applied to the textured face instead of the smooth face.

Examples 8 and 9 employed foil backings made from commercial high density polyethylene (density 0.950, melt index 12.0 g/10 minutes, injection molding grade, available from The Dow Chemical Company under the trade designation XO-5320.12 and identified in the table as "HDPE").

TABLE 1

| | EXAMPLE NUMBER | | | | | | | | | Smooth foil Control |
|---|---|---|---|---|---|---|---|---|---|---|
| | 1 | 2 | 3 | 4 | 5 | 6 | 7 | 8 | 9 | |
| Type foil | IPP | IPP | IPP | IPP | IPP | IPP | IPP | HDPE | HDPE | IPP |
| Calipered foil thickness, μm* | 254 | 259 | 208 | 266 | 206 | 145 | 206 | 341 | 226 | 127 |
| Inter-ridge spacing, μm* | 690–1220 | 365–1530 | 365–1530 | 485–1005 | 560–625 | 780–1220 | 560–625 | 690–1220 | 485–1005 | — |
| Approx. ht. difference between highest and lowest crest, μm* | ≦100 | ≦100 | ≦100 | ≦55 | ≦55 | ≦60 | ≦55 | ≦100 | ≦55 | — |
| Approx. thickness between smooth face and deepest valley, μm* | 65 | 78 | 50 | 90 | 80 | 30 | 80 | 65 | 90 | — |
| short ribs Present? | yes | no | no | no | no | yes | no | yes | no | — |
| Approx. length, μm* | 500–800 | — | — | — | — | 500–800 | — | 500–800 | — | — |
| Approx. No. per $cm^2$ | 175 | — | — | — | — | 175 | — | 175 | — | — |
| Void volume, % | 35 | 37 | 37 | 31 | 36 | 33 | 36 | 35 | 31 | 0 |
| Tensile strength parallel to ridges, N/100 mm | 437 | 385 | 350 | 360 | 273 | 207 | 273 | 256 | 261 | 262* |
| Tear perpetuation resistance perpendicular to ridges, gms | 268 | 167 | 107 | 249 | 163 | 160 | 163 | 197 | 192 | 140** |
| Stiffness 9-cm Perpendicular to ridges | 1.8 | 1.4 | 0.8 | 1.6 | 0.8 | 0.2 | 0.8 | 0.5 | 0.9 | 1.1** |
| Parallel to ridges | 5.2 | 2.1 | 1.4 | 2.3 | 1.1 | 0.7 | 1.1 | 2.3 | 2.6 | 1.2* |
| Release coating on back side | yes | yes | no | no | yes | yes | yes | yes | yes | yes |

*Measured at 90° to machine direction of foil.
**Measured in machine direction of foil.

Figure 7:
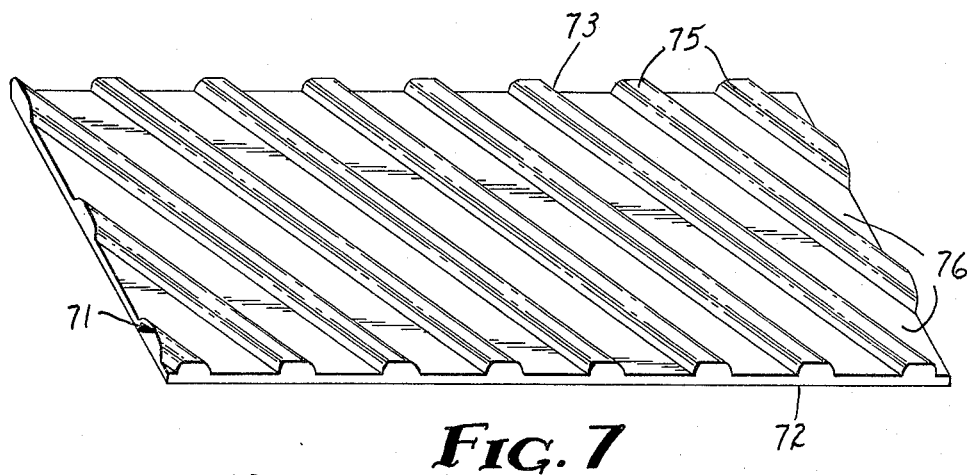
FIG. 7 is an enlarged perspective view of a foil having a different textured surface and suitable for conversion into a closure in accordance with the invention.

In FIG. 7, polymeric foil backing 71 has smooth face 72 and textured face 73, comprising crested ridges 75 and interposed valley portions 76.

EXAMPLE 10

Untensilized foil, having one smooth face and one face with the surface configuration depicted in FIG. 7, was prepared from the same isotactic polypropylene polymer described in connection with Examples 1–7. The embossed foil had a calipered thickness of 491 micrometers, ridge width of about 600 micrometers, inter-ridge spacing of about 1,200 micrometers, approximately 225 micrometers difference in height of highest and lowest crest, approximately 115 micrometers thickness between the smooth face and the bottom of the deepest valley, and an approximate void volume of 59%. In order to evaluate the relationship between ridge angle and tear perpetuation resistance, samples were cut at 10° increments and measured as described previously. Results are tabulated below:

TABLE 2

| Example No. | Angle between ridges and direction of tear perpetuation | Tear perpetuation resistance, grams | No. of tears parallel to ridges |
|---|---|---|---|
| 10A | 90° (perpendicular) | 170 | 0 |
| 10B | 80° | 186 | 0 |
| 10C | 70° | 198 | 2 |
| 10D | 60° | 118 | 5 |
| 10E | 50° | 155 | 4 |
| 10F | 40° | 136 | 5 |
| 10G | 30° | 150 | 5 |
| 10H | 20° | 139 | 5 |
| 10I | 10° | 133 | 5 |
| 10J | 0° (parallel) | 141 | 5 |

Example 10 illustrates how ridges which extend across the line of tear propagation increase the resistance to tear. When the ridges extend at angles of 60° or less to the line of tear, however, the effectiveness is greatly reduced, apparently because the tear is perpetuated along the edge of a ridge, rather than across the ridge. Further, even when a first series of ridges extends perpendicular to the line of tear, it is quite undesirable to have a second series of ridges which extends parallel to the line of tear and intersects the first series; the second series of ridges seems to greatly reduce the effectiveness of the first series of ridges.

Figure 8:
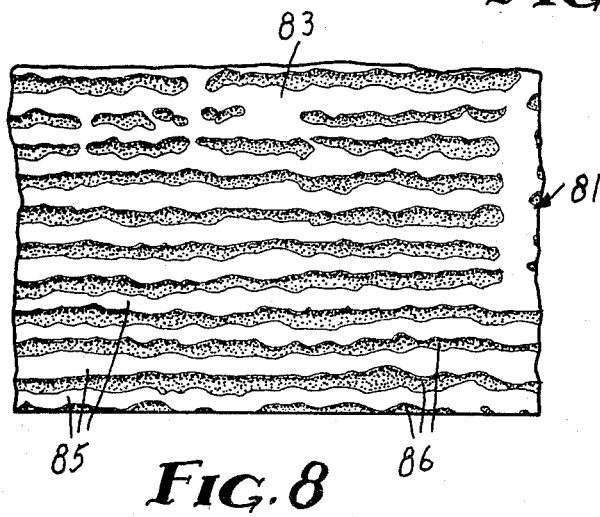
FIGS. 8-12 inclusive are enlarged view of the textured surface of other foils showing patterns suitable for closures in accordance with the invention.

In FIG. 8, polymeric foil backing 81 has one smooth face (not shown) and textured face 83, comprising crested ridges 85 and interposed valley portions 86.

Figure 9:
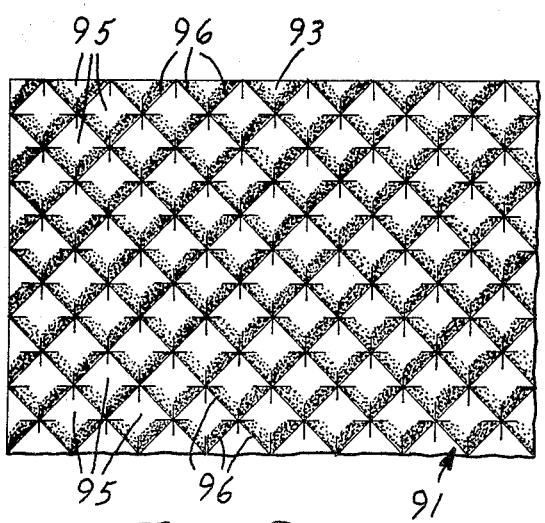

In FIG. 9, polymeric foil backing 91 has one smooth face (not shown) and textured face 93, comprising crested ridges 95 and interposed valley portions 96.

Figure 10:
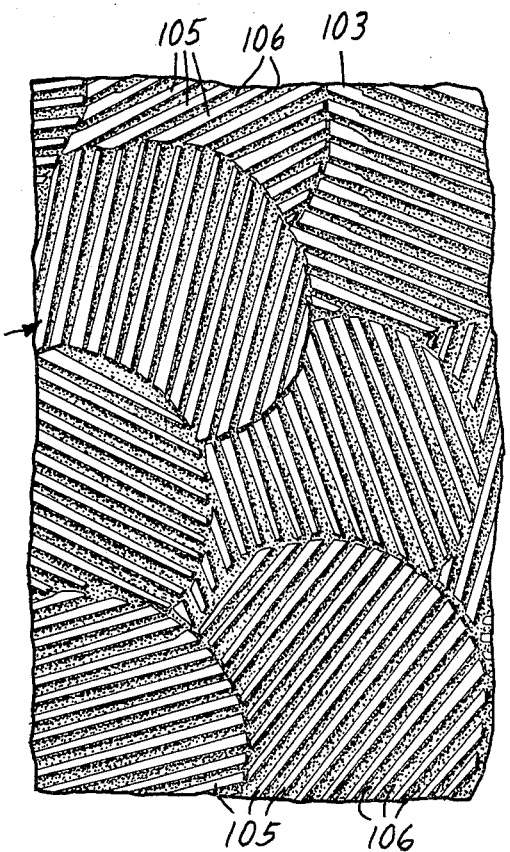

In FIG. 10, polymeric foil backing 101 has one smooth face (not shown) and textured face 103, comprising crested ridges 105 and interposed valley portions 106.

Figure 11:
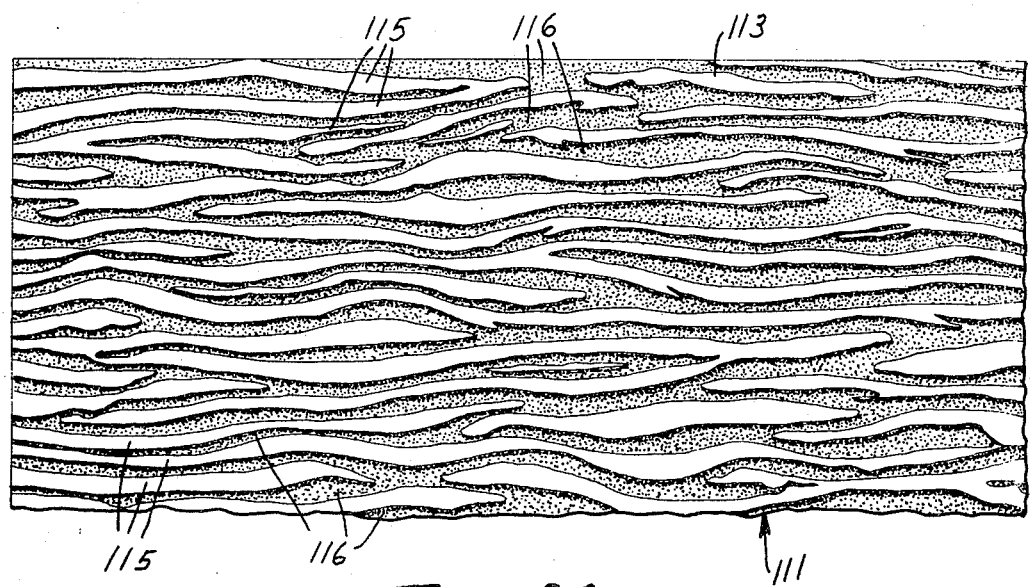

In FIG. 11, polymeric foil backing 111 has one smooth face (not shown) and textured face 113, comprising crested ridges 115 and interposed valley portions 116.

Figure 12:
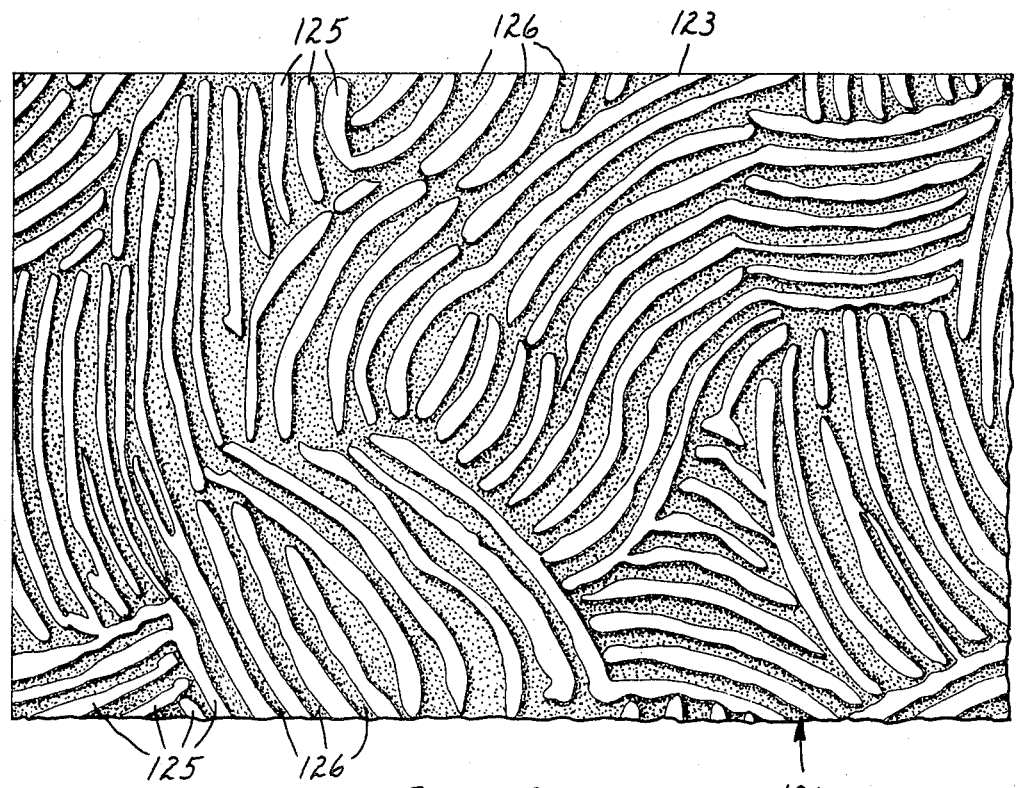

In FIG. 12, polymeric foil backing 121 has one smooth face (not shown) and textured face 123, comprising crested ridges 125 and interposed valley portions 126.

EXAMPLES 11–15

Untensilized isotactic polypropylene foil, having one smooth face and one face with the surface configuration of FIGS. 7–12, was prepared as in Examples 1–7 and 10. Physical properties were as follows:

TABLE 3

| | EXAMPLE NUMBER | | | | |
|---|---|---|---|---|---|
| | 11 | 12 | 13 | 14 | 15 |
| Calipered foil thickness, μm | 165 | 160 | 400 | 492 | 400 |
| Inter-ridge spacing, μm | 110–1517 | 695–725 | 325–1115 | 784–1933 | 300–1900 |
| Approximate ht. difference between highest and lowest crest, μm | ≦80 | ≦20 | ≦255 | ≦315 | ≦240 |
| Approximate thickness between smooth face and deepest valley, μm | 100 | 65 | 150 | 150 | 135 |
| Void volume, % | 12 | 27 | 52 | 58 | 46 |
| Tensile strength perpendicular to machine direction of foil, N/100 mm | | | 191 | 331 | 198 |
| Tear perpetuation resistance parallel to machine direction of foil, gms | 176 | 221 | 209 | 147 | 191 |
| Stiffness g-cm Parallel to machine direction of foil | 1.7 | 0.7 | 3.8 | 1.5 | 1.4 |
| Perpetuation to machine direction of foil | 1.6 | 0.7 | 2.0 | 3.0 | 2.5 |

Since many of these foils have ridges extending in more than one direction, tensile strength, tear perpetuation resistance and stiffness are all related to the machine direction of the foil as extruded. At any rate, each of these embossed foils functions satisfactorily as a backing for the diaper closure tape of the invention.

In describing the invention, particular types of textured foil backings have been mentioned. It is emphasized that the present invention is not so broad that it embraces all pressure-sensitive adhesive tapes having embossed foil backings, but is instead directed to those tapes having substantially untensilized polyolefin foil backings which possess specific physical characteristics. It will be recognized, however, that the foregoing examples are intended to be only illustrative.

I claim:

1. In the combination of a diaper and, adhered to one exterior surface thereof, at least one closure tab comprising a strip of sheet material having a coating of normally tacky and pressure-sensitive adhesive firmly bonded to one face thereof, the improvement comprising said sheet material's being a substantially untensilized, tough, ductile foil of crystalline polypropylene or linear polyethylene having a fine grain crystal structure and a calipered thickness of about 100–500 micrometers, said foil having one smooth face and one textured face, the textured face having a pattern of ridges separated by valleys, (a) the average distance between the crests of adjacent ridges being about 250–1,500 micrometers,
(b) none of said crests being more than either
  (1) 100 micrometers or
  (2) ⅔ the calipered thickness of the foil below the highest crest,
(c) the thickness of the foil between the bottom of the valleys and said smooth face being at least about 25 micrometers but not more than about ⅔ the calipered thickness, (d) the void volume included on the textured face of said foil constituting about 10–60% of the apparent volume of said foil, at least some of the ridges extending at an angle of 60° or less to the lateral edge of the closure tab and having a length significantly greater than any valleys they block, said tab being further characterized by having a tensile strength at yield of 2.5 kg/cm width, a stiffness value of no more than about 3 gm-cm perpendicular to its long dimension and no more than about 5 gm-cm parallel to its long dimension so that it is readily conformable, and a tear propagation value perpendicular to its long dimension of at least 100 grams so that it resists inadvertent edge tear resulting from tensile forces even when nicked.

2. The combination of claim 1 wherein at least one edge of the closure tab is provided with a short slit to facilitate tearing the closure when the diaper is to be removed from the wearer.

3. The combination of claim 1 or 2 wherein the pressure-sensitive adhesive is coated over the smooth face of said foil.

4. The combination of claim 3 wherein the diaper comprises a moisture-permeable inner foil liner, a moisture-absorbent central fluff layer and a moisture-impermeable outer foil.

5. The combination of claim 4 wherein the textured face also comprises short ribs extending substantially at right angles to said ridges, each of said ribs intersecting only one ridge, the ribs which intersect adjacent ridges being staggered with respect to each other, thereby minimizing any tendency of the strip to split lengthwise.

* * * * *